United States Patent
Ono et al.

(10) Patent No.: US 8,025,843 B2
(45) Date of Patent: Sep. 27, 2011

(54) HYDROGEN SENSOR

(75) Inventors: Yasuichi Ono, Miyagi-ken (JP);
Toshiaki Konno, Miyagi-ken (JP)

(73) Assignees: Alps Electric Co., Ltd., Tokyo (JP);
Honda Motor Co., Ltd., Tokyo (JP)

( * ) Notice: Subject to any disclaimer, the term of this patent is extended or adjusted under 35 U.S.C. 154(b) by 1136 days.

(21) Appl. No.: 11/112,231

(22) Filed: Apr. 22, 2005

(65) Prior Publication Data

US 2005/0258051 A1 Nov. 24, 2005

(30) Foreign Application Priority Data

Apr. 28, 2004 (JP) ................................. 2004-133339

(51) Int. Cl.
*G01N 27/00* (2006.01)
*G01N 30/96* (2006.01)
*G01N 33/00* (2006.01)

(52) U.S. Cl. .............. 422/88; 422/83; 422/98; 436/144; 436/806; 73/1.06; 73/23.2

(58) Field of Classification Search ................. 422/83, 422/88, 98; 436/144, 806; 204/431; 73/1.06, 73/23.2
See application file for complete search history.

(56) References Cited

U.S. PATENT DOCUMENTS

| | | |
|---|---|---|
| 4,608,549 A | 8/1986 | Fukui |
| 5,229,610 A * | 7/1993 | McNeil et al. ................. 250/308 |
| 5,668,301 A | 9/1997 | Hunter |
| 2005/0186696 A1 * | 8/2005 | Yamada et al. ................. 438/48 |
| 2009/0243038 A1 * | 10/2009 | Nagai et al. ................... 257/532 |

FOREIGN PATENT DOCUMENTS

| | | |
|---|---|---|
| DE | 10105581 C1 | 11/2002 |
| EP | 60211348 | 10/1985 |
| EP | 03259736 | 11/1991 |
| EP | 06148112 | 5/1994 |
| GB | 2043913 A | 10/1980 |
| JP | 3-259736 | 11/1991 |
| JP | 6-148112 | 5/1994 |
| JP | 2002-328108 | 11/2002 |
| JP | 2002-328109 | 11/2002 |

OTHER PUBLICATIONS

Kaltenpoth et al., "Multimode Detection of Hydrogen Gas Using Palladium-Covered Silicon μ-Channels," Sep. 15, 2003, Analytical Chemistry, vol. 75, No. 18.

(Continued)

*Primary Examiner* — Jill Warden
*Assistant Examiner* — Dean Kwak
(74) *Attorney, Agent, or Firm* — Beyer Law Group LLP (57) ABSTRACT

The present invention has a hydrogen detection portion composed of a semiconductor and a hydrogen absorber provided at least a part of a surface thereof, and pairs of electrodes provided at the semiconductor so as to sandwich the place at which the hydrogen absorber is provided and so as not to be electrically connected to each other with the hydrogen absorber, wherein the presence of hydrogen can be detected by the change in resistance of the semiconductor in response to hydrogen absorption into the hydrogen absorber, the change in resistance being measured between said pairs of electrodes.

9 Claims, 8 Drawing Sheets

OTHER PUBLICATIONS

Lin et al., "A novel Pd/oxide/GaAs metal-insulator-semiconductor field-effect transistor (MISFET) hydrogen sensor," Dec. 2001, Institute of Physics Publishing.

Lundstrom, et al., "A hydrogen-sensitive MOS field-effect transistor," Jan. 15, 1975, Applied Physics Letters, vol. 26, No. 2.

European Search Report date Jul. 11, 2005 from corresponding European Application No. 05009229.5.

* cited by examiner

HYDROGEN SENSOR

BACKGROUND OF THE INVENTION

1. Field of the Invention

The present invention relates to a hydrogen sensor and a method for detecting hydrogen, the hydrogen sensor being able to simply detect hydrogen at room temperature and to detect only hydrogen without receiving any influence from the presence of flammable gases such as a methane gas and an alcohol.

2. Description of the Related Art

Hitherto, gas detection elements using metal oxide semiconductors such as $SnO_2$ and $In_2O_3$ as a gas sensitive member have been known, and among the gas detection elements of this type, as an element which is devised so as to selectively detect a $H_2$ gas, for example, a hydrogen gas detection element described in Japanese Unexamined Patent Application Publication No. 3-259736 has been known.

The hydrogen gas detection element disclosed in Japanese Unexamined Patent Application Publication No. 3-259736 has the structure in which an insulating substrate, an Sn oxide layer, comb-shaped electrodes, and a catalytic layer made of palladium are sequentially provided in that order on a heating element. In a final step of forming the above element, by performing heat treatment, besides improvement in sensitivity to a $H_2$ gas, the sensitivity to gases other than a H2 gas is decreased. The hydrogen gas detection element described above has the structure in which comb-shaped Au electrodes are formed on a semiconductive Sn oxide film ($SnO_2$), and on the films mentioned above, a catalytic layer of Pd (palladium) or Pt (platinum) formed by vacuum deposition and having a mass film thickness of approximately 1 to 5 nm is provided. The hydrogen gas detection element described above responds to an ethanol gas ($C_2H_5OH$), a propane gas ($C_3H_8$), and a carbon monoxide gas (CO) besides a hydrogen gas.

In addition, as an example of a hydrogen sensor having a different structure from the above structure, for example, the structure has been proposed in which on a surface of a gas sensitive member made of a metal oxide semiconductor such as $SnO_2$ or $In_2O_3$, a thin film made of a non-flammable material such as $Al_2O_3$, $SiO_2$, or $Si_3N_4$, is formed, the thin film preventing molecules other than hydrogen from permeating therethrough and easily permitting hydrogen molecules to permeate. A hydrogen sensor having the structure described above aims to realize a highly sensitive hydrogen selective sensor by forming a dense, uniform, continuous thin film (hydrogen selective permeable film) on a surface of a gas sensitive member so as to reduce interference caused by gases other than hydrogen.

Furthermore, as a hydrogen sensor having another structure, as disclosed in Japanese Unexamined Patent Application Publication No. 6-148112, the structure has been known in which comb-shaped electrodes of Pt, a thin-film gas sensitive member of $In_2O_3$, a powdered catalyst of Pd, and a partly poisoning agent of a Si oxide adhering to the exterior surface of the powdered catalyst are provided in that order on an insulating substrate to form a laminate structure. A hydrogen gas detection element disclosed in Japanese Unexamined Patent Application Publication No. 6-148112 is formed by sputtering on the surface of the gas sensitive member and that of the powdered catalyst, and in one example of the above Japanese Unexamined Patent Application Publication, the structure has been disclosed which is formed by the steps of forming comb-shaped electrodes of Pt having a mass film thickness of 500 Å and a catalyst of Pd having a mass film thickness of 10 Å on a gas sensitive member of $In_2O_3$ having a mass film thickness of 126 Å, and on these films thus formed, further forming a partly poisoning agent (mass film thickness of 10 to 12,000 Å).

Furthermore, in test results of the example and comparative example of Japanese Unexamined Patent Application Publication No. 6-148112, it has been disclosed that the sensitivity (change in resistance) to a $H_2$ gas, a CO gas, and a $C_2H_5OH$ gas is changed in accordance with the film thickness of the partly poisoning agent and the temperature of the element. In addition, as for the temperature of the element, the measurement was performed at temperatures from 60 to 300° C.

Furthermore, in Japanese Unexamined Patent Application Publication Nos. 2002-328108 and 2002-328109, a hydrogen sensor has been disclosed having the structure in which an insulating layer incorporating a heating element is provided on a silicon substrate, comb-shaped electrodes and a gas sensitive film are further provided thereon, and on this gas sensitive film, catalyst clusters and a partly poisoning agent are dispersed.

According to the hydrogen gas detection element disclosed in Japanese Unexamined Patent Application Publication No. 2002-328108, the structure has been disclosed in which an insulating layer incorporating a heater is laminated on a silicon substrate, a gas sensitive film of $SnO_2$ or $In_2O_3$ or of an oxide semiconductor primarily composed thereof is formed on the above insulating layer, comb teeth-shaped electrodes are disposed at an interface between this gas sensitive film and the insulating layer thereunder, catalyst clusters of a noble metal such as Pd are dispersed on the upper surface side of the gas sensitive film, and a powdered partly poisoning agent of Si is dispersed on the upper surface of the gas sensitive film and the catalyst clusters at the surface side thereof. In addition, Japanese Unexamined Patent Application Publication No. 2002-328108 disclosed that $TiO_2$, ZnO, $Cu_2O$, NiO, FeO, $WO_3$, and the like may be used as the oxide semiconductor forming the gas sensitive film. According to description of performance evaluation, in a sample in which catalyst clusters (thickness of 2 nm) of Pd and a partly poisoning agent (Si film thickness of 2, 20, 50 nm) of a Si oxide film are formed on a gas sensitive film (thickness of 7, 13, 20 nm) of $SnO_2$, detection of a hydrogen gas can be efficiently performed in a state heated to 220° C. In Japanese Unexamined Patent Application Publication No. 2002-328109, in the structure similar to that in Japanese Unexamined Patent Application Publication No. 2002-328108, the invention has been disclosed in which the film thickness of the partly poisoning agent is specified in a particular range.

The conventional hydrogen gas sensors described in Japanese Unexamined Patent Application Publication Nos. 3-259736, 6-148112, 2002-328108, and 2002-328109 each have been well known as a sensor using the following basic principle. According to this basic principle, when the reducing gases (flammable gases) described above act on an oxide semiconductor material such as $SnO_2$ or $In_2O_3$, since the reducing gases serve to pull oxygen out of the oxide semiconductor material, and hence electrons trapped with oxygen are allowed to remain in the semiconductor, the thickness of an electrical depletion layer is decreased, and a region in which charged carriers are present is increased, thereby causing the change in resistance. The technique described above relate to a technique in which the selectivity of hydrogen is improved as much as possible by decreasing influence of flammable gases other than hydrogen.

However, in consideration of the above basic operation principle, the hydrogen gas sensors having the conventional structure surely also react with reducing gases other than hydrogen, and hence a problem has occurred in that it is not possible to selectively detect only hydrogen. In addition, the hydrogen gas sensors of the conventional structure each have a problem in that after the hydrogen sensor once reacts with a hydrogen gas, in an environment other than an oxygen-containing environment such as the atmospheric environment or an oxygen gas environment, the resistance of the sensor is not allowed to return to an original level. For example, there has been a problem in that the sensors described above cannot be used when detection of hydrogen is to be continuously and repeatedly performed in an environment in which oxygen is not present, such as an inert gas environment.

Furthermore, since the hydrogen sensors having the conventional structure described above use a reaction between an oxide material and a reducing gas, the sensitivity tends to be improved at a high temperature, such as 200 to 300° C. Hence, a heater is generally incorporated in the hydrogen sensor so that detection operation is performed in a heated state, and in other words, this type of hydrogen sensor is difficult to be used at room temperature. In addition, for detection operation, since the oxide material must be heated to a high temperature, electricity must be applied to the heater, and as a result, electric power consumption is disadvantageously increased.

In addition, in the hydrogen sensors having the conventional structure described above, after hydrogen gas is depleted, although it is intended to allow the resistance to return to an original level in an oxygen environment, the resistance will not ideally return to the original level, and hence a problem has arisen in that repetitive use of this type of sensor itself is difficult to be performed. The reason for this has been believed that since gas detection is performed while the oxide material is being heated, oxidation of the oxide material is advanced by oxygen in air, and hence the resistance does not return to a predetermined initial value after detection of gases is performed, thereby causing drift of the output value.

SUMMARY OF THE INVENTION

The present invention was made in consideration of the situations described above, and an object of the present invention is to provide a hydrogen sensor and a method for detecting hydrogen, the hydrogen sensor being able to detect a hydrogen gas at room temperature, to be operated without heating, to have an electrical power-saving structure, to be repeatedly used after hydrogen detection is once completed, and to be used for a long period of time.

According to one aspect of the present invention, there is provided a hydrogen sensor comprising a hydrogen detection portion composed of a semiconductor and a hydrogen absorber provided at at least a part of a surface of the semiconductor, and a pair of electrodes provided at the semiconductor so as to sandwich the place at which the hydrogen absorber is provided and so as not to be electrically connected to each other with the hydrogen absorber. In this hydrogen sensor described above, the presence of hydrogen gas is detected by the change in resistance of the semiconductor in response to hydrogen absorption into the hydrogen absorber, the change in resistance being measured between said pair of electrodes.

As the hydrogen absorber, a material composed of a metal may be used, and when being simply formed into a film, a metal hydrogen absorber has a resistance much lower than that of the semiconductor and is placed in an electrical conduction state, resulting in significant decrease in resistance of the semiconductor between the pair of electrodes. Hence, when being formed on the semiconductor, the hydrogen absorber is formed to have a thickness smaller than that forming a film in which particles are connected to each other, so that the hydrogen absorber is put in a non-conduction state. That is, a hydrogen absorber in a non-electrical conduction state in which particles are dispersed in the form of islands is formed on the semiconductor. On the semiconductor provided with the hydrogen absorber in a dispersed state in which particles thereof are independently dispersed, when the electrodes are separately provided so as to sandwich the particles in a dispersed state, and the resistance of the semiconductor between the pair of electrodes is measured, the hydrogen absorption into the hydrogen absorber influences the semiconductor layer, the resistance thereof is changed thereby, and as a result, detection of hydrogen can be performed.

This hydrogen detection can be performed without heating, and in addition, the resistance of the semiconductor easily returns to the original level after hydrogen is eliminated from the hydrogen absorber. Hence, since measurement can be repeatedly performed and can be performed at room temperature without heating, compared to the conventional hydrogen sensors, an electrical power-saving structure can be formed.

According to the present invention, the semiconductor described above may be a layer-shaped semiconductor provided on an insulating substrate.

As the semiconductor, when a layer-shaped material provided on the insulating substrate is used, a semiconductor having a required thickness can be easily formed on the insulating substrate by a film forming method such as deposition or sputtering, and miniaturization of the hydrogen sensor can also be easily performed.

According to the present invention, the hydrogen absorber may be provided at the surface of the semiconductor so as to be in contact therewith.

The hydrogen absorber is preferably formed so as to be in direct contact with the surface of the semiconductor, and by the direct contact therewith, hydrogen absorbed into the hydrogen absorber directly influences the semiconductor, and as a result, the change in resistance can be reliably detected.

According to the present invention, the hydrogen absorber may be provided at the surface of the semiconductor with a thin-film insulating layer interposed therebetween.

When the hydrogen absorber is formed at the surface of the semiconductor, instead of direct formation of the hydrogen absorber thereon, the thin-film insulating layer may be formed therebetween. When absorbing hydrogen, the hydrogen absorber formed above the semiconductor with the thin-film insulating layer interposed therebetween influences the semiconductor through the thin-film insulating layer and changes the resistance of the semiconductor. Also in this case, as is the case described above, since the resistance is changed by the presence of hydrogen, detection of hydrogen can be performed. In addition, when the thin-film insulating layer is formed on the surface of the semiconductor, a protective function for the surface of the semiconductor can be secured.

According to the present invention, an exposed surface of the hydrogen detection portion may be covered with a hydrogen permeable film through which hydrogen permeates.

Hydrogen in environment reaches the hydrogen absorber through the hydrogen permeable film through which hydrogen permeates and is absorbed into the hydrogen absorber, thereby causing the change in resistance of the semiconductor. In addition, when covering the hydrogen absorber, the hydrogen permeable film serves as a protective film for the hydrogen detection portion.

According to the present invention, room-temperature operation can be performed, and no change in resistance between the electrodes occurs by the presence of a flammable gas, such as a methane gas, a propane gas, and ethyl alcohol.

According to the conventional hydrogen sensors using a semiconductor oxide and a catalyst, in addition to detection of hydrogen, reaction simultaneously occurs by the presence of a flammable gas, such as a methane gas, a propane gas, and ethyl alcohol, and as a result, the change in resistance of the semiconductor oxide occurs. However, according to the structure of the present invention, no change in resistance between the electrodes occurs by the presence of a flammable gas, such as a methane gas, a propane gas, and ethyl alcohol. Hence, a hydrogen sensor can be provided which is not influenced by the presence of other gases and which can detect only hydrogen as a measurement object.

According to the present invention, operation can be performed in an oxygen-free environment, and a resistance of the semiconductor, which is changed from an initial state due to hydrogen absorption into the hydrogen absorber, can return to the initial state by elimination of hydrogen from the hydrogen absorber.

By the elimination of hydrogen from the hydrogen absorber, since the resistance returns to the initial state, an effect can be obtained in which the hydrogen sensor can be repeatedly used after hydrogen detection is performed once. In this case, after the elimination of hydrogen, without performing heat treatment or oxidation treatment, the hydrogen sensor may only be placed in a hydrogen-free environment. Since hydrogen is eliminated from the hydrogen absorber when the hydrogen sensor is simply placed in a hydrogen-free environment, the hydrogen sensor can be repeatedly used without performing any particular treatment for forcedly eliminating hydrogen from the hydrogen absorber.

According to the present invention, the semiconductor may be a non-oxide semiconductor.

In the present invention, the non-oxide semiconductor may be a non-oxide semiconductor primarily composed of one of Si (silicon), SiC (silicon carbide), Ge (germanium), SiGe (silicon germanium), GaAs (gallium arsenide), GaN (gallium nitride), and C (diamond).

It is believed that when the aforementioned semiconductor is used, the change in resistance which occurs by the presence of hydrogen absorbed in the hydrogen absorber is not caused by a reaction mechanism in which the change in thickness of the electrical depletion layer occurs along with an oxidation or a reduction reaction including hydrogen as in the case of an oxide type semiconductor. On the other hand, it may be estimated that by a resistance-change mechanism different from that caused by an oxidation or a reduction reaction, the mobility of electrons in the semiconductor is influenced, and that as a result, the resistance is changed.

According to the present invention, it is preferable that the hydrogen absorber be composed of one of Pd, a Pd alloy, Pt, and a Pt alloy and be arranged on the semiconductor to have a dispersed island structure.

In the present invention, as the hydrogen permeable film, a silicon nitride, a silicon oxide, or a polyimide may be used.

In accordance with another aspect of the present invention, there is provided a method for detecting hydrogen, having the step of measuring the change in resistance of a semiconductor caused by hydrogen absorption into a hydrogen absorber which is provided at a surface of the semiconductor, whereby the presence of hydrogen is detected.

In accordance with still another aspect of the present invention, there is provided a method for detecting hydrogen, having the step of measuring at room temperature the change in resistance of a semiconductor caused by hydrogen absorption into a hydrogen absorber, wherein a pair of electrodes is provided on the semiconductor, and the hydrogen absorber is provided between the electrodes on the semiconductor and has a dispersed island structure composed of one of Pd, a Pd alloy, Pt, and a Pt alloy, whereby the presence of hydrogen is detected.

In the present invention, at two sides of the position at which the hydrogen absorber is provided on the semiconductor, the pair of electrodes is provided so as not be electrically connected to each other with the hydrogen absorber, and from the change in resistance of the semiconductor caused by hydrogen absorption into the hydrogen absorber, which is measured by the above pair of electrodes, the presence of hydrogen is detected. Hence, the change in resistance generated by influence on the semiconductor, which is resulting from the hydrogen absorption into the hydrogen absorber, can be reliably detected, and as a result, detection of hydrogen can be performed.

DESCRIPTION OF THE PREFERRED EMBODIMENTS

First Embodiment

Next, an embodiment of a hydrogen sensor according to the present invention will be described with reference to figures.

In all the following figures, in order to facilitate understanding thereof, the film thicknesses and dimensional ratios of individual constituent elements are optionally changed.

Figure 1:
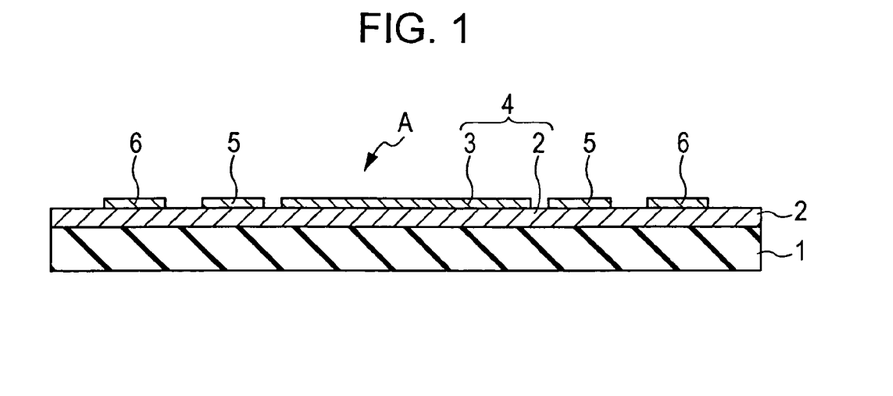
FIG. 1 is a side view of a hydrogen sensor according to a first embodiment of the present invention.
Figure 2:
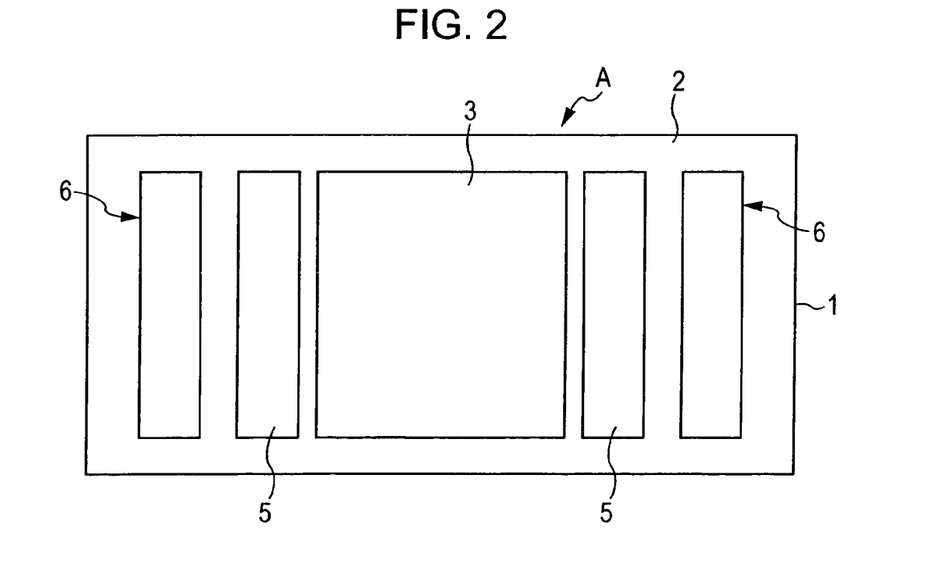
FIG. 2 is a plan view of the same hydrogen sensor as mentioned above.

FIGS. 1 and 2 are views showing the structure of the first embodiment of a hydrogen sensor according to the present invention, and a hydrogen sensor A of this embodiment has the following structure. That is, on the approximately entire upper surface of an insulating substrate (insulating base body) 1, a semiconductor layer (semiconductor) 2 is provided, and at a central portion on the upper surface of this semiconductor layer 2, a hydrogen absorber 3 is formed in which particles are dispersed and arranged in the form of islands. In addition, inside electrodes 5 and 5 and outside electrodes 6 and 6 are provided on the surface of the semiconductor layer 2, the inside electrodes 5 and 5 being located at two sides of the hydrogen absorber 3, the outside electrodes 6 and 6 being located at two sides of the inside electrodes 5 and 5 so as to be further from the center. In the structure of this embodiment, the semiconductor layer 2 and the hydrogen absorber 3 form a hydrogen detection portion 4.

The insulating substrate (insulating base body) 1 may be a substrate formed of an insulating material, and for example, as the substrate, there may be mentioned a glass and a quartz substrate, such as $SiO_2$, a ceramic substrate such as $Al_2O_3$, and a Si substrate used as an insulating substrate which is not doped with ions. Since this insulating substrate 1 may only have insulating properties at an upper surface side thereof, a conductive substrate provided with an insulating layer on the surface thereof may also be used.

The semiconductor layer 2 has a layer shape formed of a semiconductor, such as ITO (indium tin oxide), GaN, or an n-type Si doped with P. As this semiconductor layer 2, a semiconductor material formed by doping an intrinsically insulating material with ions is preferably used. As this type of semiconductor, for example, there may be used an n-type semiconductor formed by doping ions of a V-group element, such as P, As, or Sb, into silicon, or a p-type semiconductor formed by doping ions of a III-group element such as B into silicon. In addition to those mentioned above, as another semiconductor forming the semiconductor layer 2, an n-type or a p-type SiC, Ge, SiGe, GaAs, or GaN may also be used.

The hydrogen absorber (hydrogen absorbing material member) 3 preferably has the structure in which particles made of Pd, a Pd alloy, Pt, or a Pt alloy, particles made of another platinum-group element, or particles of an alloy made of the aforementioned element are dispersed and arranged in the form of islands. This hydrogen absorber 3 absorbs hydrogen when being placed in an installation environment in which hydrogen is present, and on the contrary, the hydrogen absorber 3 releases absorbed hydrogen when hydrogen is depleted in the installation environment.

In addition, besides the metals mentioned above, of course, an alloy containing La, Ti, Zr, Mg, a rare earth metal, Ca, V, or the like, which is generally known as an hydrogen absorbing alloy, may also be used.

In this embodiment, the hydrogen absorber 3 is composed of a hydrogen-absorbing material, such as the aforementioned metal or the alloy thereof, and when a film is formed on the semiconductor layer 2 using the hydrogen-absorbing material, a pattern thereof must be formed so that electrodes to be formed in a subsequent step are not electrically connected to each other. When the pattern is formed, a photolithographic method is preferably used. As another structure, the state is preferably formed in which particles are dispersed in the form of islands which are isolated from each other so that electrical conductivity is not obtained as a whole.

In FIGS. 1 and 2, this hydrogen absorber 3 is simply shown in the form of a film. In the pattern shown in FIGS. 1 and 2, since the hydrogen absorber 3 is provided at a distance from the electrodes, the effect of the present invention can be obtained even when a continuous film is formed; however, the hydrogen absorber 3 is preferably formed to have a thickness so as to function as an insulating member. That is, when being magnified, this insulating layer is an aggregate preferably made of particles separately dispersed in the form of islands. For example, it is preferable that as the hydrogen absorber 3, an insulating member having a resistance of approximately 1 $M\Omega$ be used, and that the thickness of the hydrogen absorber 3 be in the range of approximately 0.5 to 5 nm.

The hydrogen absorber 3 dispersed in the form of islands can be formed using a film-forming method, such as a vacuum deposition method or a sputtering method, in which when particles are deposited on the semiconductor layer 2, the film formation is stopped in a state before the particles are formed into a film. For example, since being a good electrically conductive material, when Pd, a Pd alloy, Pt, or a Pt alloy is formed into a film, a conductive member is formed. Hence, when the film formation is stopped in an insulating state which is obtained before the film is formed, the hydrogen absorber 3 can be formed on the semiconductor layer 2 to have a dispersed island structure in which a plurality of particles is dispersed and arranged in the form of islands. Accordingly, when being formed to have a thickness in the range described above, the hydrogen absorber 3 can be formed on the semiconductor layer 2 as an insulating member. In this structure, the hydrogen absorber 3 has a longitudinal length slightly smaller than that of the insulating substrate 1 and has a lateral length one severalth of that of the insulating substrate 1. Hence, at the two sides of the hydrogen absorber 3 shown in FIGS. 1 and 2 in the lateral direction, the semiconductor layer 2 is exposed.

The inside electrodes 5 described above are formed on the upper surface of the semiconductor layer 2 so as to be disposed at the two sides of the hydrogen absorber 3 with spaces therefrom. The inside electrodes 5 are composed of a good conductive metal material such as Au or Al and are formed by a film-forming method such as a vacuum deposition method, a sputtering method, or a screen-printing method. The outside electrodes 6 described above are formed at two end sides of the semiconductor layer 2 so as to sandwich the inside electrodes 5 and 5 from the two sides thereof.

In detecting hydrogen using the hydrogen sensor A formed as described above, the hydrogen sensor A is placed in a measurement environment and is used for measurement of the change in electrical resistance of the semiconductor layer 2 itself by measuring the voltage between the inside electrodes 5 and 5 while a predetermined current is applied between the outside electrodes 6 and 6. In this case, what measured by the inside electrodes 5 and 5 corresponds to the change in electrical resistance of the semiconductor layer 2 itself.

When a hydrogen gas is present in an installation environment of the hydrogen sensor A, hydrogen is absorbed into the hydrogen absorber 3 of the hydrogen sensor A, the state of charged carriers in a part of the semiconductor layer 2 in contact with the hydrogen absorber 3 is changed by hydrogen absorption into the hydrogen absorber 3, and due to this change, the resistance of the semiconductor layer 2 is changed. In addition, when hydrogen is depleted in the installation environment of the hydrogen sensor A of this example, since hydrogen is released from the hydrogen absorber 3, the resistance of the semiconductor layer 2 returns to the original level, and hence the hydrogen sensor is ready to be again used. From the state described above, when hydrogen is again allowed to be present in this installation environment, since the change in resistance of the semiconductor layer 2 occurs, the hydrogen sensor A of this example can be repeatedly used.

The installation environment of the hydrogen sensor A may be room temperature, and in addition, even in an environment at a temperature slightly higher than that, any problem may not occur. Although conventional hydrogen sensors are generally operated at a high temperature and cannot be reused when reoxidation is not performed at a high temperature such as approximately 200 to 300° C. after detection of hydrogen, the hydrogen sensor A having the above structure can be reused when being simply placed in a room-temperature environment after detection of hydrogen.

Second Embodiment

Figure 3:
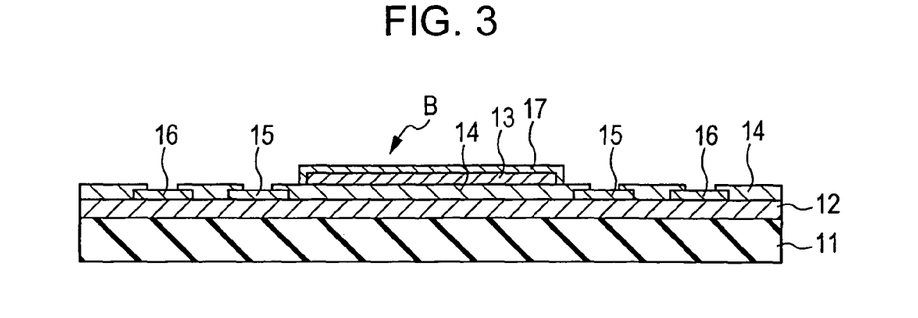
FIG. 3 is a side view of a hydrogen sensor according to a second embodiment of the present invention.
Figure 4:
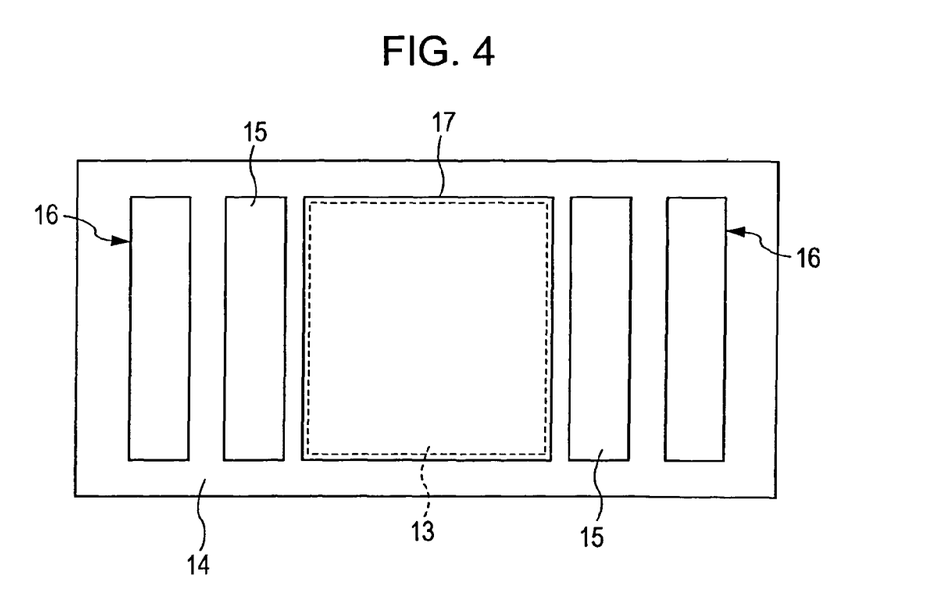
FIG. 4 is a plan view of the same hydrogen sensor as mentioned above.

FIGS. 3 and 4 are views showing the structure of the second embodiment of a hydrogen sensor according to the present invention, and a hydrogen sensor B of this embodiment has the following structure. That is, on the approximately entire upper surface of an insulating substrate II, a semiconductor layer 12 is provided, and inside electrodes 15 and 15 and outside electrodes 16 and 16 are formed at places located at two sides of a central portion on the upper surface of this semiconductor layer 12, the places being equivalent to those of the case of the hydrogen sensor A of the above first embodiment when viewed in plan. In addition, a thin-film insulating layer 14 is provided so as to cover the peripheral portions of the electrodes 15 and 16 and the other areas, that is, the upper surface of the semiconductor layer 12, and a hydrogen absorber 13 having the structure in which particles are dispersed and arranged in the form of islands is formed so as to be located at the central portion of the upper surface side of the semiconductor layer 12 when viewed in plan. Furthermore, a hydrogen permeable protective film 17 is formed so as to cover the hydrogen absorber 13.

The hydrogen absorber 13 of this embodiment is formed of a material equivalent to that of the hydrogen absorber 3 of the first embodiment described above, and the size and the shape thereof are formed to be equivalent to those described above. The inside electrodes 15 of this embodiment are also formed of a material equivalent to that of the inside electrodes 15 of the first embodiment described above, and the size and the shape thereof are formed to be equivalent to those described above. In the same manner as described above, the outside electrodes 16 of this embodiment are also formed of a material equivalent to that of the outside electrodes 16 of the first embodiment described above, and the size and the shape thereof are formed to be equivalent to those described above.

The hydrogen sensor B of this second embodiment can be used in the same manner as that of the hydrogen sensor A of the first embodiment described above. That is, when the hydrogen sensor B is installed in an environment at room temperature or an environment in which a temperature slightly higher than that is required, and a hydrogen gas is present in this installation environment, hydrogen is absorbed into the hydrogen absorber 13 through the protective film 17, and as a result, the resistance of the semiconductor layer 12 is changed. In this embodiment, the thin-film insulating layer 14 provided between the semiconductor layer 12 and the hydrogen absorber 13 must have a thickness so as not to interfere with the influence on the semiconductor layer 12 which is generated by hydrogen absorption into the hydrogen absorber 13.

Hence, in the thin-film insulating layer 14, at least a part thereof which is used as an underlying layer for the hydrogen absorber 13 preferably has a thickness in the range of approximately 1 to 100 nm.

As is the case of the hydrogen sensor A of the first embodiment, when being measured by a four-terminal method using the outside electrodes 16 and 16 and the inside electrodes 15 and 15, the change in resistance of the semiconductor layer 12 described above can be accurately measured, and hence hydrogen can be detected.

Heretofore, in the above embodiments, the case in which the semiconductor in the form of a film is provided on the substrate to form the hydrogen detection portion was described by way of example; however, the form of the semiconductor as the hydrogen detection portion is not limited to a film. For example, the following structure may be formed in which a massive semiconductor or a molded semiconductor having a desired shape formed by compacting semiconductor particles is provided, a pattern of a hydrogen absorber is provided, which does not allow a pair of electrodes to be electrically connected to each other, on a part of the massive semiconductor or the molded semiconductor, and subsequently, inside electrodes and outside electrodes are formed so as to detect the resistance of the semiconductor which is the massive semiconductor or the molded semiconductor.

EXAMPLES

Example 1

An ITO film (indium tin oxide film) having a thickness of 0.01 µm was formed on a glass substrate 16 mm long and 9 mm wide, and at a central portion of this ITO film, an island-shaped hydrogen absorber film of Pd was formed having a thickness of 12 Å and having a rectangular shape 5 mm long and 7 mm wide. The film of this hydrogen absorber was an insulating member on the glass substrate.

Subsequently, inside electrodes (inside electrodes each having a laminate structure formed of a Ti layer as an underlayer and a Au layer provided thereon) having a size of 1.2 by 7.5 mm made of a Ti/Au layer were first formed on the ITO film and at two sides of the hydrogen absorber with spaces therefrom, and furthermore, outside electrodes made of a Ti/Au layer were formed outside of the inside electrodes at a distance of 1 mm therefrom.

The hydrogen sensor having this structure was placed in a measuring chamber, and a repetitive hydrogen gas-detection test was performed in which, at a temperature of 30° C. (approximately room temperature), the atmospheric environment (100% of air) and a hydrogen gas-containing air environment (1% of a hydrogen gas and 99% of air) were alternately switched over therebetween at every predetermined time interval. The result is shown in FIG. 5.

Figure 5:
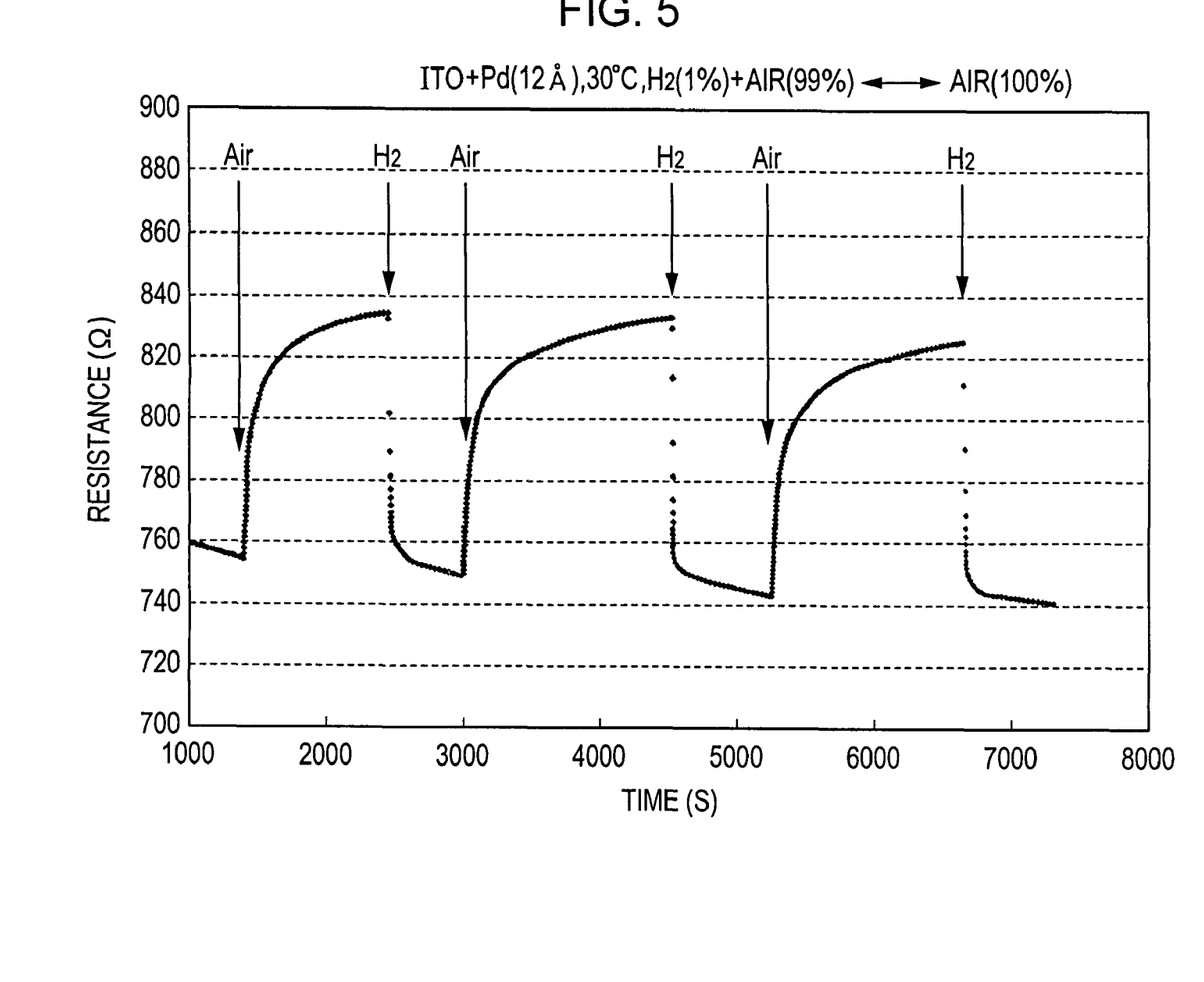
FIG. 5 is a graph showing the change in resistance obtained when, by using a hydrogen sensor of an example structure in which a hydrogen absorber of Pd having a thickness of 12 Å is provided on an ITO film used as a semiconductor layer, an environment in which this hydrogen sensor is placed is repeatedly switched over between an Ar gas environment containing 1% of a hydrogen gas and a 100% atmospheric environment.

From the result shown in FIG. 5, when the atmospheric environment was switched over to the hydrogen gas-containing air environment, the resistance was immediately decreased, and hence it was found that a hydrogen gas can be reliably, repeatedly, and reproducibly detected. In addition, after being switched over to the hydrogen gas-containing air environment, when the environment was allowed to return to the atmospheric environment, it is apparent that the resistance is rapidly increased and returns to an approximately constant range (800 to 840Ω), and hence it is also apparent that this hydrogen sensor is suitable for repetitive use.

Furthermore, since this reaction is confirmed by a measurement result at 30° C. which is approximately room temperature, heating is not necessarily performed using a heating element, and as a result, compared to the conventional hydrogen sensor performing measurement while being necessarily heated by a heater, it is apparent that the electrical power consumption can be decreased, the oxidation of the hydrogen absorber is unlikely to occur since operation is performed at room temperature, and hence a long life can be obtained.

Example 2

Figure 6:
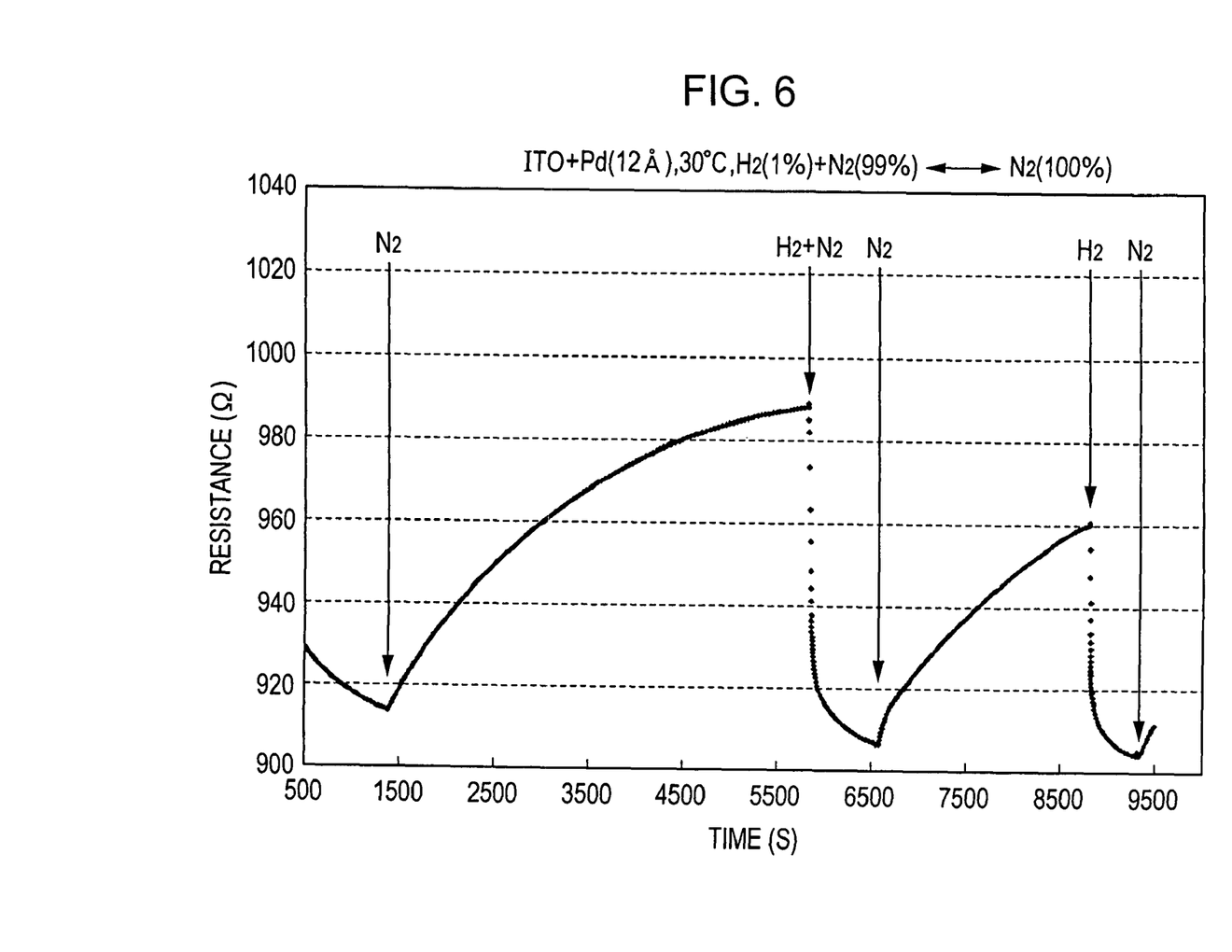
FIG. 6 is a graph showing the change in resistance obtained when, by using a hydrogen sensor of an example structure in which a hydrogen absorber of Pd having a thickness of 12 Å is provided on an ITO film used as a semiconductor layer, an environment in which this hydrogen sensor is placed is repeatedly switched over between a nitrogen gas environment containing 1% of a hydrogen gas and a 100% nitrogen gas environment.

FIG. 6 is a graph showing the change in resistance in the case in which a hydrogen sensor having the same structure as that of the hydrogen sensor in Example 1 described above was used. In this example, at a temperature of 30° C., the environment in the chamber in which this hydrogen sensor was placed was repeatedly and alternately switched over between a nitrogen gas environment containing 1% of a hydrogen gas and a 100% nitrogen gas environment.

From the result shown in FIG. 6, it was found that when the 100% nitrogen gas environment is switched over to the nitrogen gas environment containing 1% of a hydrogen gas, the resistance is immediately decreased, and that a hydrogen gas can be reliably, repeatedly, and reproducibly detected. In addition, it is apparent that after being switched over to the nitrogen gas environment containing a hydrogen gas, when the environment is again allowed to return to the 100% nitrogen gas environment, the resistance is rapidly increased and returns to the original value. Accordingly, it is also apparent that the hydrogen sensor is suitable for repetitive use and that the life thereof can be increased.

Furthermore, since this reaction is confirmed by a measurement result at 30° C. which is approximately room temperature, heating using a heating element is not required, and compared to the conventional hydrogen sensor performing measurement while being necessarily heated by a heater, it is apparent that the electrical power consumption can be decreased, the oxidation of the hydrogen absorber is unlikely to occur since operation is performed at room temperature, and hence a long life can be obtained.

From the results thus obtained, the hydrogen sensor of the present invention and the hydrogen sensor having the conventional structure are compared with each other for further investigation.

A hydrogen sensor using a conventional oxide semiconductor has been realized by the mechanism in which detection of hydrogen is performed by using a redox reaction, and the detection of hydrogen is performed using a phenomenon in which when a part of the semiconductor is reduced by hydrogen adsorption to form a state in which oxygen is removed, the thickness of the electrical depletion layer of the oxide semiconductor is changed, and as a result, the resistance is changed. Hence, after hydrogen is detected once, the oxide semiconductor must be oxidized by heating to a high temperature so that the reduced part thereof is allowed to return to the original state. However, in consideration of the test results described above, according to the hydrogen sensor of the present invention, even when the environment returns to a 100% nitrogen gas environment, the resistance returns to the original level. Hence, in the hydrogen sensor of the present invention, the change in resistance of the semiconductor layer is not caused by a redox reaction, and the change in resistance is caused, by an electrical conduction mechanism of the semiconductor layer on which the hydrogen absorption into the hydrogen absorber directly acts. Accordingly, it is apparently found that, in the hydrogen sensor of the present invention, the mechanism in which the resistance of the semiconductor is changed is completely different from that of the conventional hydrogen sensor.

Example 3

Figure 7:
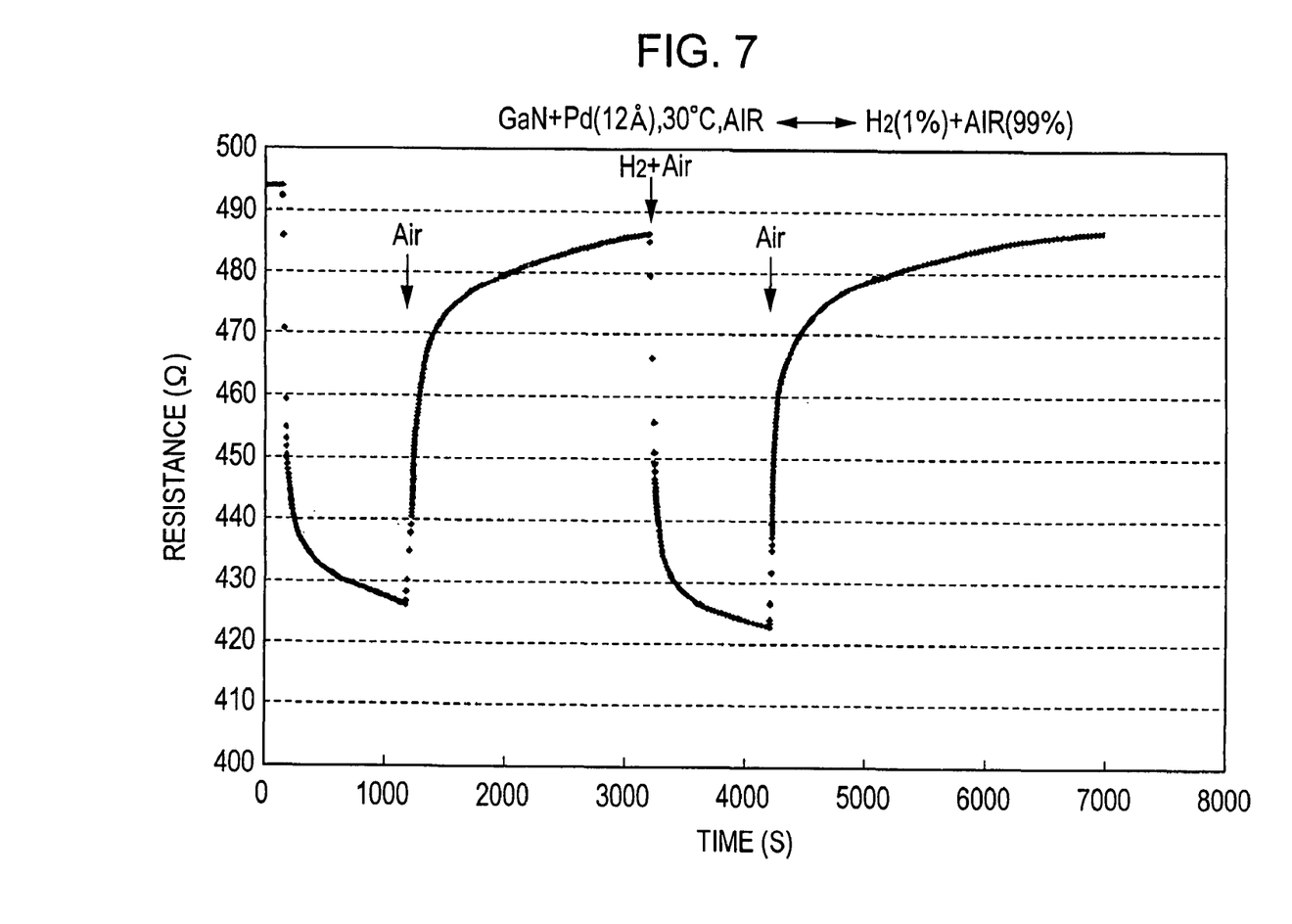
FIG. 7 is a graph showing the change in resistance obtained when, by using a hydrogen sensor of an example structure in which a hydrogen absorber of Pd having a thickness of 12 Å is provided on a GaN film used as a semiconductor layer, an environment in which this hydrogen sensor is placed is repeatedly switched over between an atmospheric environment containing 1% of a hydrogen gas and a hydrogen-free atmospheric environment.

FIG. 7 is a graph showing the change in resistance of a hydrogen sensor having the structure in which a hydrogen absorber of Pd having a thickness of 12 Å was provided on a GaN (Si doped) film having a thickness of 1 μm used as the semiconductor layer (the thickness and the size of the substrate, electrode, and hydrogen absorber were the same as those in Example 1), the change in resistance being obtained when the environment in the chamber in which this hydrogen sensor was placed was repeatedly and alternately switched over between an atmospheric environment containing 1% of a hydrogen gas and a 100% atmospheric environment at a temperature of 30° C.

From the result shown in FIG. 7, it was found that when the 100% atmospheric environment is switched over to the atmospheric environment containing a hydrogen gas, the resistance is immediately decreased, and that the presence of a hydrogen gas can be reliably, repeatedly, and reproducibly detected. In addition, it is apparent that after being switched over to the atmospheric environment containing a hydrogen gas, when the environment is again allowed to return to the 100% atmospheric environment, the resistance is rapidly increased and returns to an approximately constant range (480 to 490Ω). Accordingly, it is also apparent that the hydrogen sensor is suitable for repetitive use and the life thereof can be increased.

Furthermore, since this reaction is confirmed by a measurement result at a temperature of 30° C. which is approximately room temperature, heating using a heating element is not required, and compared to the conventional hydrogen sensor performing measurement while being necessarily heated by a heater, it is apparent that the electrical power consumption can be decreased, the oxidation of the hydrogen absorber is unlikely to occur since operation is performed at room temperature, and hence a long life can be obtained.

Example 4

Figure 8:
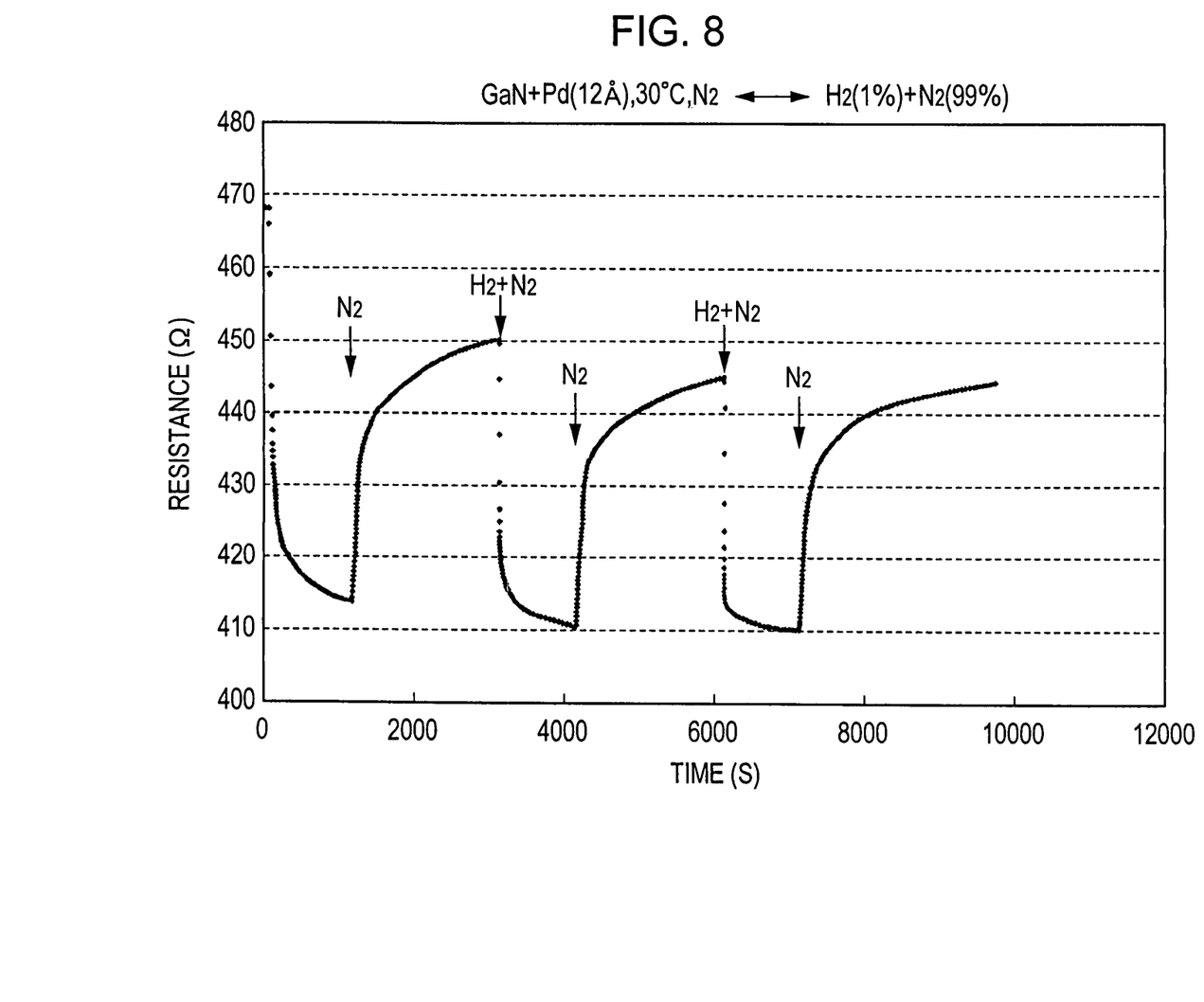
FIG. 8 is a graph showing the change in resistance obtained when, by using a hydrogen sensor of an example structure in which a hydrogen absorber of Pd having a thickness of 12 Å is provided on a GaN film used as a semiconductor layer, an environment in which this hydrogen sensor is placed is repeatedly switched over between a nitrogen gas environment containing 1% of a hydrogen gas and a 100% nitrogen gas environment.

FIG. 8 is a graph showing the change in resistance of a hydrogen sensor having the structure in which a hydrogen absorber of Pd having a thickness of 12 Å was provided on a GaN (Si doped) film having a thickness of 1 μm used as the semiconductor layer (the thickness and the size of the substrate, electrode, and hydrogen absorber were the same as those in Example 1), the change in resistance being obtained when the environment in the chamber in which this hydrogen sensor was placed was repeatedly and alternately switched over between a nitrogen gas environment containing 1% of a hydrogen gas and a 100% nitrogen gas environment at a temperature of 30° C.

From the result shown in FIG. 8, it was found that when the 100% nitrogen gas environment is switched over to the nitrogen gas environment containing a hydrogen gas, the resistance is immediately decreased, and that a hydrogen gas can be reliably, repeatedly, and reproducibly detected. In addition, it is apparent that after being switched over to the nitrogen gas environment containing a hydrogen gas, when the environment is again allowed to return to the 100% nitrogen gas environment, the resistance is immediately increased and returns to an approximately constant range (440 to 450Ω). Accordingly, it is also apparent that the hydrogen sensor is suitable for repetitive use and the life thereof can be increased.

Furthermore, since this reaction is confirmed by a measurement result at a temperature of 30° C. which is approximately room temperature, heating using a heating element is not required, and compared to the conventional hydrogen sensor performing measurement while being necessarily heated by a heater, the electrical power consumption can be apparently decreased. In addition, also in this example, since the resistance returned to the original level when the environment was set to the 100% nitrogen gas environment containing no hydrogen, it is apparent that the resistance of the semiconductor layer is changed by a mechanism different from that of the conventional hydrogen sensor.

Example 5

Figure 9:
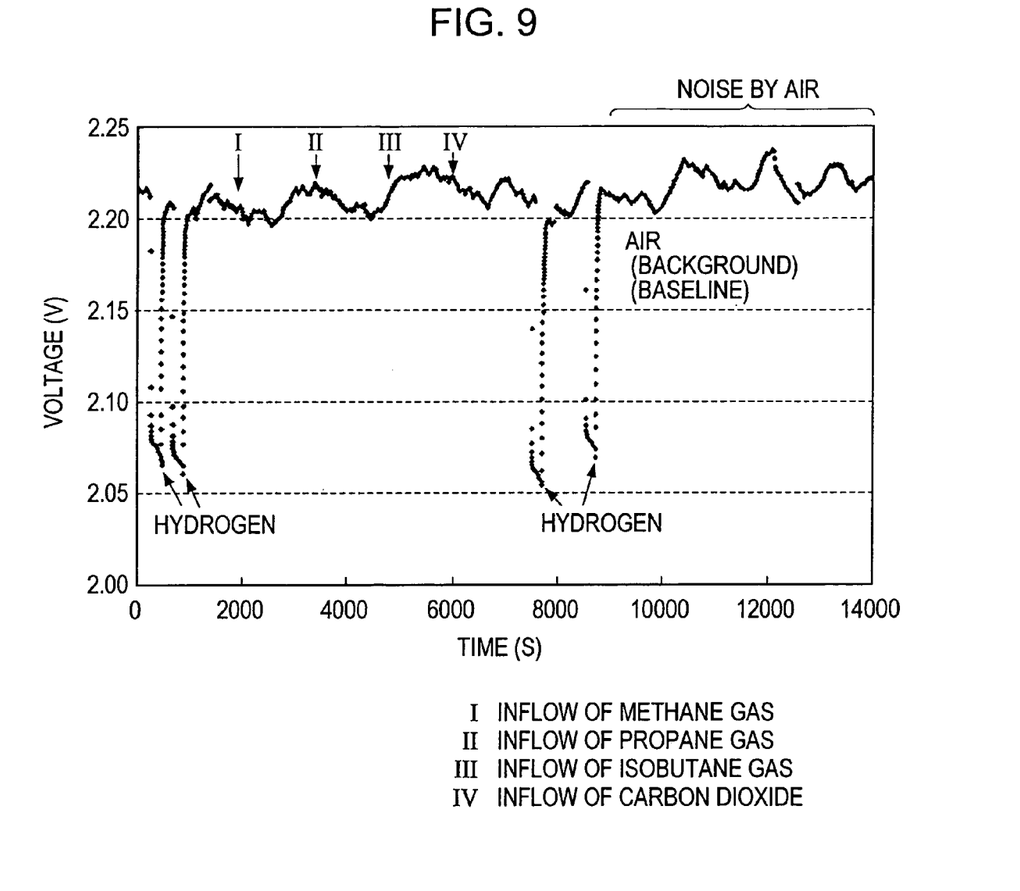
FIG. 9 is a graph showing a result of voltage measurement by a four-terminal method obtained when a hydrogen gas, a methane gas, a propane gas, an isobutane gas, and carbon dioxide are sequentially detected by a hydrogen sensor of the present invention.

FIG. 9 is a graph showing the result of the change in resistance of a hydrogen sensor having the structure in which a hydrogen absorber of Pd having a thickness of 12 Å was provided on a GaN (Si doped) film having a thickness of 1 μm used as the semiconductor layer (the thickness and the size of the substrate, electrode, and hydrogen absorber were the same as those in Example 1), the change in resistance being obtained when the environment in the chamber in which this hydrogen sensor was placed was changed as described below. That is, the change in resistance was obtained by switching over twice between an atmospheric environment containing 0.5% of a hydrogen gas and a 100% atmospheric environment at a temperature of 130° C.; subsequently, the change in resistance was obtained by supplying gases other than hydrogen, that is, a methane gas (10,000 ppm), a propane gas (10,000 ppm), an isobutane gas (10,000 ppm), and carbon dioxide (8,000 ppm), into the chamber in a time sequential manner, and then allowing the environment to return to the atmosphere after the supply of each of the aforementioned gases; the change in resistance was then obtained by switching over twice between an atmospheric environment containing 0.5% of a hydrogen gas and a 100% atmospheric environment at a temperature of 130° C.; and next, a noise component was measured while 100% of air was simply allowed to flow.

From the result shown in FIG. 9, it was found that in the hydrogen sensor of the present invention, even when a methane gas, a propane gas, an isobutane gas, and carbon dioxide are allowed to flow in the environment, the change in resistance is very small so as to be hardly discriminated from the noise component caused by air, and that when hydrogen is supplied, since a rapid change in resistance occurs, only hydrogen can be clearly detected.

In addition, under the same conditions as those of Example 5, instead of the gases mentioned above, carbon monoxide (1,000 ppm), an ammonium gas (100 ppm), and air (highly humid air at room temperature) passing through water at a temperature 23° C. were also supplied, the same result as that shown in FIG. 9 was obtained. Hence, it was confirmed that the hydrogen sensor does not react with the aforementioned gases and air and reacts with only hydrogen.

Accordingly, unlike the hydrogen sensor having the conventional structure using an oxide semiconductor, the hydrogen sensor of the present invention has an ability of detecting only hydrogen.

Comparative Example

Figure 10:
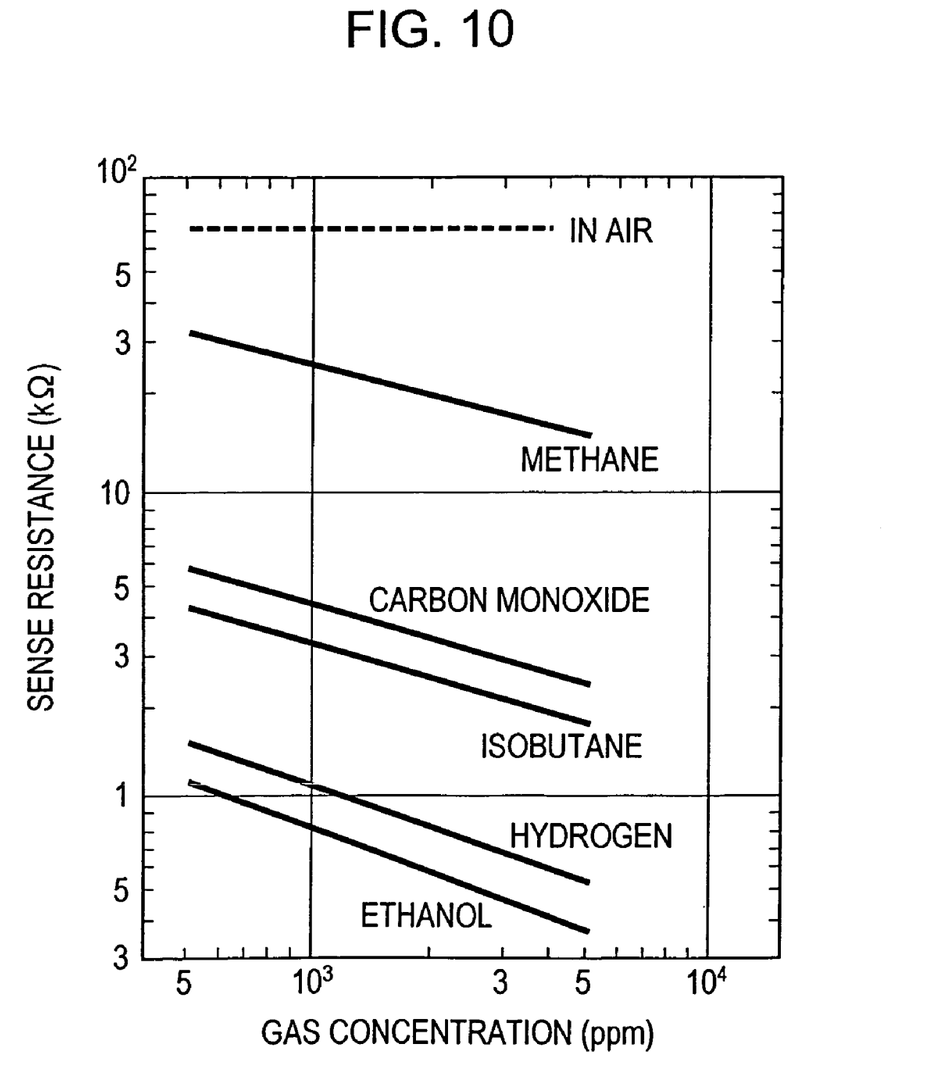
FIG. 10 is a graph showing the change in resistance with a gas concentration obtained when a conventional oxide semiconductor type hydrogen sensor reacts with various gases.

FIG. 10 is a graph showing typical examples of sensitivity of a gas sensor to various gases, the gas sensor having a conventional structure using an $SnO_2$ oxide semiconductor (for example, see "Densi Zairyo Ceramic" (Electronic Material Ceramic), first edition, p. 128, published by Ohmsha Ltd.).

As a material for a semiconductor gas sensor, an n-type oxide semiconductor (semiconductor using electrons as charge carriers), such as $SnO_2$ or ZnO, has been primarily used, and the material mentioned above is used in the form of a sintered body or a film. The mechanism of detecting a flammable gas is currently understood as follows.

On a surface of an oxide semiconductor placed in air, oxygen is generally adsorbed. This adsorbed oxygen pulls electrons out of the semiconductor and are adsorbed as a negative charge, and hence, in the case of an n-type semiconductor, an electrical depletion layer having a thickness of several to several tens nanometers is formed in the surface thereof. By this depletion layer, the electrical resistance of the surface is increased, and as a result, the electron transfer between particles and in the film is prevented. The adsorbed oxygen ions are in the form of $O^-$ or $O^{2-}$ at a temperature of 200 to 400° C. at which the sensor is to be used. When a flammable gas is present in this case, the adsorbed oxygen reacts therewith.

For example, in the case of carbon monoxide, since a reaction represented, for example, by $CO+O^-$ (adsorbed oxygen)$\rightarrow CO_2+e^-$ (electron), occurs, the amount of adsorbed oxygen is decreased and hence the thickness of the electrical depletion layer is decreased, and as a result, a conduction channel is formed with a low resistance part of an adjacent particle. Hence, a phenomenon occurs in which the electrical resistance of the entire semiconductor is extremely decreased. As shown in FIG. 10, in the relationship between the concentration of various gases and the electrical resistance of a gas sensor of this type using an n-type semiconductor, the gas sensitivity is generally increased as the number of carbons is increased. The reason for this is that the consumption of adsorbed oxygen is increased as the number of carbons is increased.

A reaction theory of a general semiconductor gas sensor has been construed as described above, and this type of semiconductor sensor surely reacts with the various gases as shown in FIG. 10 besides hydrogen. On the other hand, as described in the above examples, the hydrogen sensor according to the present invention reacts with only hydrogen without receiving any influence from other gases, and even when this hydrogen sensor is operated in an oxygen-free environment and is then allowed to return to a 100% nitrogen gas environment which contains no oxygen, the resistance thereof returns to the original level. From the comparison described above, it is apparent that the hydrogen sensor of the present invention is operated in accordance with a mechanism completely different from that for the sensor using an oxide semiconductor described in the conventional example.

What is claimed is:
1. A hydrogen sensor comprising:
a non-oxide semiconductor in a form of a thin-film layer, the semiconductor having a resistance;

a hydrogen absorber provided over the semiconductor, the hydrogen absorber and a part of the semiconductor underneath thereof forming a hydrogen detection portion, wherein the resistance of the semiconductor changes in response to hydrogen absorption into the hydrogen absorber; and a pair of electrodes for measuring a change in the resistance of the semiconductor, the pair of electrodes being provided on the semiconductor on each side of the hydrogen absorber so as to sandwich the hydrogen absorber therebetween, wherein each of the electrodes is spaced apart from the hydrogen absorber such that the electrodes are not in direct contact with the hydrogen absorber, and wherein the electrodes are configured to electrically connect to the hydrogen absorber only through the semiconductor.

2. The hydrogen sensor according to claim 1, wherein the hydrogen absorber is provided on the surface of the semiconductor so as to be in contact therewith.

3. The hydrogen sensor according to claim 1, wherein the hydrogen absorber is provided over the surface of the semiconductor with a thin-film insulating layer interposed therebetween.

4. The hydrogen sensor according to claim 1, wherein an exposed surface of the hydrogen detection portion is covered with a hydrogen permeable film which allows hydrogen to permeate therethrough.

5. The hydrogen sensor according to claim 1, wherein the non-oxide semiconductor is a non-oxide semiconductor primarily composed of one element selected from the group consisting of silicon, silicon carbide, germanium, silicon germanium, gallium arsenide, gallium nitride, and carbon (diamond).

6. The hydrogen sensor according to claim 1, wherein the hydrogen absorber is composed of one element selected from the group consisting of palladium, a palladium alloy, platinum, and a platinum alloy, and is arranged on the semiconductor to have a dispersed island structure.

7. The hydrogen sensor according to claim 4, wherein the hydrogen permeable film is composed of an element selected from the group consisting a silicon nitride, a silicon oxide, and a polyimide.

8. The hydrogen sensor according to claim 1, wherein the pair of electrodes includes:

a pair of inner electrodes for measuring the resistance of the semiconductor, the pair of inner electrodes sandwiching the hydrogen absorber therebetween; and a pair of outer electrodes for providing a predetermined current therebetween while the resistance is being measured, the pair of outer electrode sandwiching the hydrogen absorber and the pair of the inner electrodes therebetween.

9. The hydrogen sensor according to claim 1, wherein a thickness of the thin-film semiconductor layer is about 0.1 μm to 1 μm.

* * * * *